United States Patent [19]

Bancroft

[11] 3,963,021

[45] June 15, 1976

[54] RESPIRATORS

[75] Inventor: Barrie Bancroft, Dronfield, near Sheffield, England

[73] Assignee: Secretary of State for Trade and Industry in Her Britannic Majesty's Government of the United Kingdom of Great Britain and Northern Ireland, London, England

[22] Filed: July 9, 1974

[21] Appl. No.: 486,856

[30] Foreign Application Priority Data

Jan. 16, 1974 United Kingdom................. 2095/74

[52] U.S. Cl........................... 128/145 R; 128/142.7; 128/146.6; 128/142.6; 2/171.3

[51] Int. Cl.[2]............................................. A61F 9/06

[58] Field of Search.......... 128/145 R, 142.5, 142.6, 128/142.7, 146; 2/3 R, 171.3

[56] References Cited

UNITED STATES PATENTS

| | | | |
|---|---|---|---|
| 1,075,906 | 10/1913 | Duncan et al. | 128/142.7 |
| 2,896,617 | 7/1959 | Gibbons | 128/142.7 |
| 3,168,748 | 2/1965 | Limberg | 2/171.3 |
| 3,258,010 | 6/1966 | Austin et al. | 128/142.7 |
| 3,293,659 | 12/1966 | Shepard | 128/142.7 |
| 3,413,972 | 12/1968 | Depping | 128/142.7 |
| 3,813,696 | 6/1974 | Yeager | 2/171.3 |
| 3,822,698 | 7/1974 | Guy | 128/142.7 |

FOREIGN PATENTS OR APPLICATIONS

| | | | |
|---|---|---|---|
| 74,773 | 5/1954 | Netherlands | 128/142.6 |

*Primary Examiner*—Robert W. Michell
*Assistant Examiner*—Henry J. Recla
*Attorney, Agent, or Firm*—Cameron, Kerkam, Sutton, Stowell & Stowell

[57] ABSTRACT

A respirator which is in the form of a protective hood is arranged to fit over the head including the face of a wearer, leaving a space between the hood and the wearer's head. A sealing member is provided between the hood and the back and sides of the wearer's head with means normally fitted within the hood to supply filtered air which can pass over the wearer's head and down over the wearer's face.

6 Claims, 2 Drawing Figures

RESPIRATORS

Figure 1:
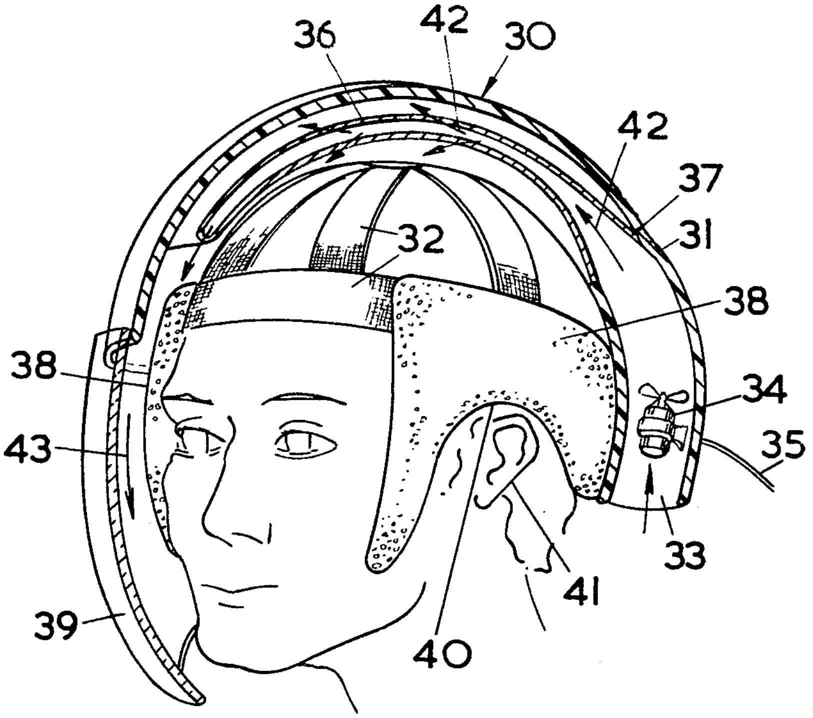

This invention relates to respirators, more especially powered respirators for use in a dusty environment.

At a Symposium entitled "Technical Measures of Dust Prevention in Mines" held in Luxembourg in October 1972, a powered respirator hood was described in which air was arranged to be drawn forward between the hood and an inner skin through a filter and down over the wearer's face. Such a hood has been found to be difficult to construct and hot to wear. The hood also had a flexible skirt at shoulder level so that the gap between the hood and the wearer's body was minimised, thus also minimising the risk of unfiltered, dusty air reaching the wearers face from below. However, the skirt may be disadvantageous in confined conditions when maximum freedom of movement of the head relative to the shoulders is required. A British patent application covering the hood was filed on May 9, 1972 as No 21584/72.

It is an object of the present invention to overcome the above-listed disadvantages of the previously disclosed respirator hood.

According to the invention, a respirator comprises a hood having support means by which it can fit over the head of a wearer and be supported so as to leave a space between the hood and the wearer's head, sealing means attached to the hood and arranged so as to form, in use, a seal between the hood and the back and sides of the wearer's head, and means to supply filtered air which can pass over and in contact with the wearer's head and down over the wearer's face to escape at the lower forward edge of the hood. The hood generally conforms to the shape of the wearer's head and can be used without a shoulder length skirt so that the hood can be worn in confined working situations.

The sealing means may be, for example, a band of flexible expanded plastics material, and may also form a seal down the sides of the wearer's face.

The means to supply filtered air may comprise a filter fitted in said space between the hood and the wearer's head and an air displacing device by which, in use, air can be propelled through the filter. The filter may be of large surface area and occupy a major portion of the space between the hood and the top of the wearer's head, may be, for example, a bag filter, and may be made of any conventional filter material such as a resin-treated wood felt.

Optionally the filter may be of sufficiently large area to allow an adequate supply of air to be drawn or propelled through it by means of a low-power air displacing device such as an electrically driven fan powered by a cap lamp battery attached to the hood or to a belt round the wearer. Because the power required to drive the fan is low, the cap lamp battery may still provide power for a miner's cap lamp or similar lamp attached to the hood.

The air displacing device may be advantageously arranged at the rear of the hood so that it does not increase the height of the hood above the top of the head of the wearer, or project to any material extent beyond the rear of the hood.

The filter may have sound-absorptive properties to reduce the noise from the fan reaching the wearer. Additional sound absorptive material may be incorporated as a lining to the hood. The filter may be produced at a low cost, and further advantages are that the filter may be protected from damage by the outer skin of the hood.

In another form, the means to supply filtered air may be an air supply hose connected to a remote source - the hose is preferably connected to the rear of the hood.

The hood may have a visor which can be opened if required, the outer skin of the hood may be a helmet which is sufficiently strong to protect the wearer from falling or obstructing bodies, and the support means may be conventional helmet-supporting harness.

It is an advantage of a respirator according to the invention that it is relatively simple to construct, that the passage of air over the top of the wearer's head provides a cooling effect and that there is minimum restriction of head movement. In the form utilising a battery driven air displacing device, the need for a trailing air hose or electric cable is eliminated. Such a respirator is particularly suitable for use in dusty environments such as a coal mine or foundry, especially in confined spaces.

When the sealing means is extended down the sides of the wearer's face, the gap at the lower edge of the hood through which air escapes can be very small so that the chance of dusty air entering the hood from below is minimised. If required, an exhalation valve can be provided at the lower edge to further reduce the risk. Alternatively, a flexible skirt attached to the lower edge of the hood can be provided reducing the gap still further although the skirt may restrict head movement somewhat.

Figure 2:
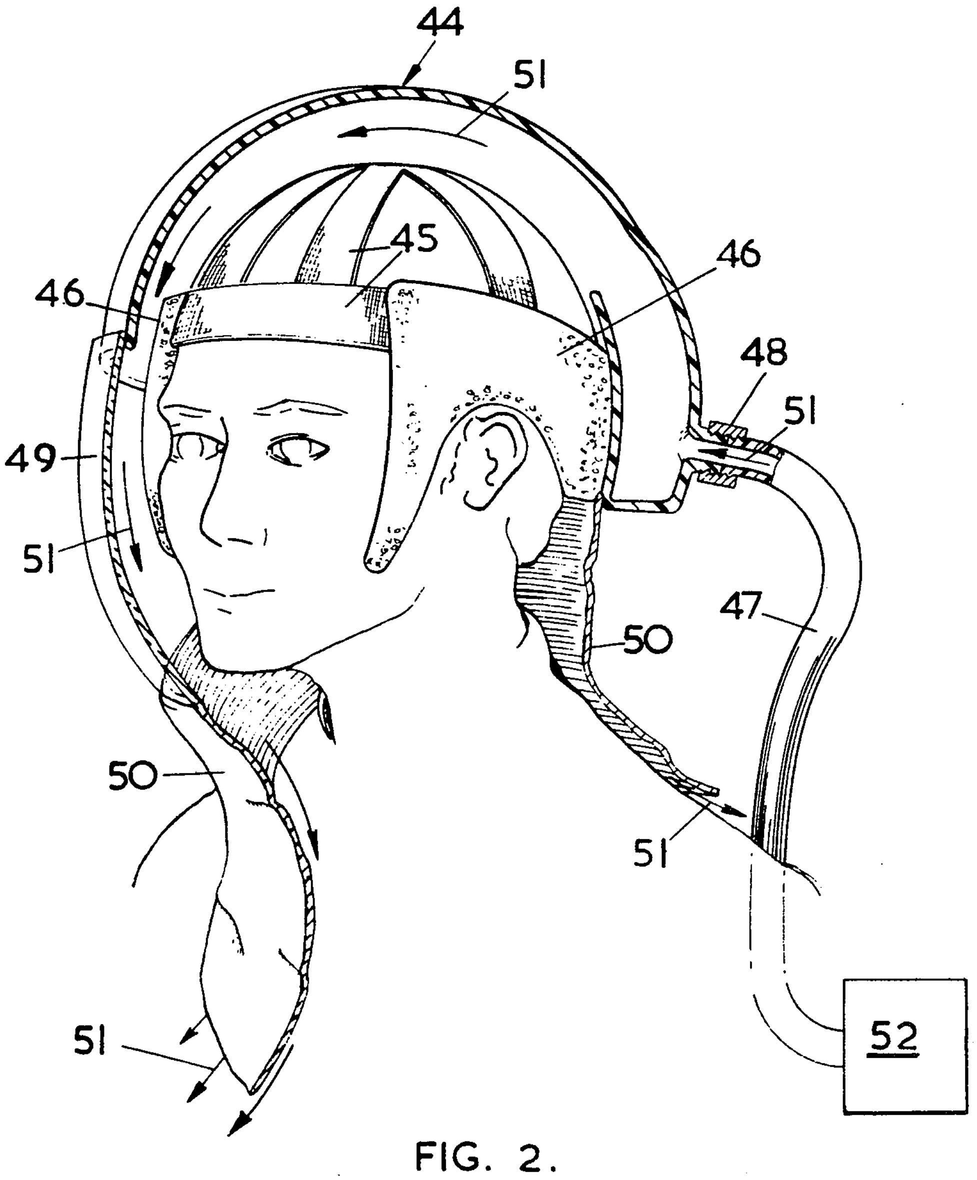

The invention will now be described by way of example only with reference to the accompanying drawings in which:

FIG. 1 is a diagrammatic front to rear cross sectional view of one form of respirator as worn; and FIG. 2 is a similar view of an alternative respirator In FIG. 1, a hood indicated generally by reference numeral 30 comprises an outer rigid skin 31, a hood-supporting harness 32 and an air inlet 33. A fan 34 is situated near the air inlet 33 and is connected by lead 35 to a cap lamp battery (not shown). A bag filter 36 is attached at its mouth 37 to the outer skin 31 and to the supporting harness 32 and is arranged to lie between the outer skin 31 and the top of the wearer's head.

A band of expanded polyurethane 38 is attached to the outer skin 31 and forms a seal at the back and sides of the wearer's head and down the sides of the wearer's face. The hood has a visor 39 (which may be either fixed or pivoted so as to be openable) and the outer skin is shaped at 40 to remain clear of the wearer's ear 41.

In operation, the fan 34 propels dusty air through the inlet 33, through the filter mouth 37, and through the filter 36 as indicated by the arrows 42. The dust is retained by the filter 36 and clean air indicated by the arrow 43 flows past the face of the wearer and escapes at the bottom edge of the visor 39. The flexible band 38 prevents air from escaping at the sides or rear of the wearer's head.

In FIG. 2, a hood indicated generally by reference numeral 44 has a support harness 45 and a band of expanded polyurethane 46. From a remote source of filtered air 52 an air hose 47 is connected by connecting means 48 to the rear of the hood. To the lower edge of the hood 44 and a fixed visor 49 is connected a flexible skirt 50. In use, air passes along the hose, over the top of the wearer's head, down past the wearer's face, and escapes at the lower edge of the flexible skirt, as indicated by the arrows 51.

It will be easily understood that some of the features of the respirators shown in FIGS. 1 and 2 are interchangeable. For example, the flexible skirt 50 may be used in a respirator having a filter 36 and fan 34, and the air hose 47 may be used in a respirator which does not have a flexible skirt 50. .

A respirator according to the invention will have the usual advantages of powered respirators, i.e. positive pressure to minimize leakage of dusty air into the hood, a flow of air past the wearer's face to increase comfort, and additionally there is no contact between the respirator and sensitive portions of the wearer's face. Speech communication may be only slightly impaired by the visor and hearing is completely unimpaired. Since almost the whole of the wearer's head is covered by the respirator, the wearer is protected from flying particles such as may occur in a mine.

I claim:

1. A respirator comprising:

a helmet having a top, front, side and rear portions and including only two domed structural layers located one within the other, one of said layers being an apertured support harness for engagement on the head of a wearer, said other layer being an impermeable outer hood structure, and said two layers being sealingly connected to each other along said side portions of said helmet but otherwise located in spaced relation defining therebetween a single open-ended domed passageway extending between the front portion and rear portion of said helmet;

a bag-form filter having a void-forming body predominantly defined by two opposed similarly domed sides, and having a mouth at an edge portion of said sides affording access to said void, said filter extending in said passageway from said rear portion to said front portion and being sealingly connected around its mouth at a location adjacent said rear portion between said helmet layers to laterally fill a rear portion of said passageway with said mouth opening towards the rear portion of said helmet and with said body extending through said passageway in generally conforming disposition therewith towards the front portion of said helmet;

and powered air displacement means connected with the rear portion of said helmet and communicating with said passageway to pass air forcibly through said passageway, by way of said filter, from the rear portion to the front portion of said helmet.

2. A respirator according to claim 1 wherein said air displacement means comprises an electrically powered fan mounted on said helmet and located in said passageway between said filter mouth and the rear portion of said passageway.

3. A respirator according to claim 1 comprising a resilient sealing member extending downwardly from said support structure adjacent the side and rear portion of said helmet for engagement with corresponding areas of a wearer's head, said member having a free edge and being arched upwardly below the side portions of said helmet to circumscribe the wearer's ears.

4. A respirator according to claim 2 comprising a visor having opposing side edges and a lower edge projecting downwardly from the front of said hood structure, said side edges of said visor being sealingly connected with said sealing member.

5. A respirator according to claim 1 wherein said air displacement means comprises a remote source of pressurised air and an air supply hose connected between said source and the rear portion of said hood structure; and further comprising a visor projecting downwardly from the front portion of said hood structure, and a flexible skirt connected to the lower portion of said hood structure and the lower edge of said visor.

6. A respirator comprising:

a helmet having top, front, rear and side portions and including only two domed structural layers located one within the other, one of said layers being an apertured support harness for engagement on the head of a wearer, said other layer being an impermeable outer hood structure, means for sealingly connecting said two layers to each other along said side portions but otherwise located in spaced relation defining therebetween a single open-ended domed passageway extending between the front portion and rear portion of said helmet;

a bag-form filter having a void-forming body predominantly defined by two opposed similarly domed sides, and having a mouth at an edge portion of said sides affording access to said void, said filter extending in said passageway from said rear portion to said front portion and being sealingly connected around its mouth to the periphery of said passageway between said helmet layers at a location adjacent said rear portion to laterally fill a rear portion of said passageway with said mouth opening towards the rear portion of said helmet and with said body extending through said passageway in generally conforming disposition therewith towards the front portion of said helmet;

a visor having opposing side edges and a lower edge projecting downwardly from the front portion of said hood structure;

said means for sealingly connecting said two layers comprising a resilient sealing member extending downwardly from said support harness structure adjacent the side and rear portion of said helmet for engagement with corresponding areas of a wearer's head, said member having a lower free edge being arched upwardly below the side portions of said helmet to circumscribe the wearer's ears, said member further including front edges facing the front portion of said helmet and being sealingly connected to said opposing side edges of said visor to extend said passageway across the face of the wearer;

and a battery-operated electric fan mounted on said helmet and located in said passageway between said filter mouth and the rear portion of said passageway.

* * * * *